(12) United States Patent
Hocking et al.

(10) Patent No.: US 10,881,495 B2
(45) Date of Patent: Jan. 5, 2021

(54) EMBOLI CAPTURE DEVICE

(71) Applicant: ACCESS POINT TECHNOLOGIES, INC., Tokyo (JP)

(72) Inventors: Gordon Donald Hocking, Tokyo (JP); Zhenghui Cheng, Guangdong (CN)

(73) Assignee: ACCESS POINT TECHNOLOGIES, INC., Tokyo (JP)

( * ) Notice: Subject to any disclaimer, the term of this patent is extended or adjusted under 35 U.S.C. 154(b) by 305 days.

(21) Appl. No.: 15/739,572

(22) PCT Filed: Jun. 29, 2015

(86) PCT No.: PCT/JP2015/068635
§ 371 (c)(1),
(2) Date: Jul. 3, 2018

(87) PCT Pub. No.: WO2017/002155
PCT Pub. Date: Jan. 5, 2017

(65) Prior Publication Data
US 2018/0311029 A1 Nov. 1, 2018

(51) Int. Cl.
*A61F 2/01* (2006.01)
*A61F 2/24* (2006.01)

(52) U.S. Cl.
CPC .......... *A61F 2/013* (2013.01); *A61F 2/011* (2020.05); *A61F 2/2427* (2013.01);
(Continued)

(58) Field of Classification Search
CPC .. A61F 2/013; A61F 2/2427; A61F 2002/011; A61F 2002/015; A61F 2002/016; A61F 2210/0014
See application file for complete search history.

(56) References Cited

U.S. PATENT DOCUMENTS

2004/0153117 A1* 8/2004 Clubb .................. A61F 2/01
606/200
2010/0114017 A1* 5/2010 Lenker ............... A61B 17/1214
604/96.01
(Continued)

FOREIGN PATENT DOCUMENTS

CN 102670277 A 9/2012
JP 2011-525405 A 9/2011
(Continued)

OTHER PUBLICATIONS

PCT/ISA/210, "International Search Report for International Application No. PCT/JP2015/068635" dated Sep. 29, 2015.

*Primary Examiner* — Erich G Herbermann
(74) *Attorney, Agent, or Firm* — Manabu Kanesaka

(57) ABSTRACT

A filter device includes: a shaft having an intermediate coil wire between a proximal filter wire and a distal filter wire; a proximal filter on the proximal filter wire; and a distal filter on the distal filter wire. The intermediate coil wire is disposed to extend between downstream and upstream blood vessels to pass through a path of placement that leads to another downstream blood vessel. Both the filters have a contracted configuration for being delivered into the blood vessel and an expanded configuration for capturing an embolus inside the blood vessel. The proximal filter is oriented such that an inlet opening, for taking in the embolus, of a proximal filter body in the expanded configuration faces the distal side, and the distal filter is oriented such that an inlet opening, for taking in the embolus, of a distal filter body in the expanded configuration faces the proximal side.

8 Claims, 8 Drawing Sheets

(52) U.S. Cl.
 CPC ... *A61F 2002/015* (2013.01); *A61F 2002/016* (2013.01); *A61F 2210/0014* (2013.01)

(56) References Cited

U.S. PATENT DOCUMENTS

| | | |
|---|---|---|
| 2010/0185231 A1 | 7/2010 | Lashinski |
| 2012/0172915 A1* | 7/2012 | Fifer .................. A61F 2/013 606/200 |
| 2013/0238010 A1 | 9/2013 | Johnson et al. |
| 2014/0249565 A1 | 9/2014 | Laine |

FOREIGN PATENT DOCUMENTS

| | | |
|---|---|---|
| JP | 2013-027593 A | 2/2013 |
| JP | 2015-510788 A | 4/2015 |
| WO | 2011/034718 A2 | 3/2011 |

\* cited by examiner

EMBOLI CAPTURE DEVICE

RELATED APPLICATIONS

The present applications claim priority from International Application No. PCT/JP2015/068635, filed Jun. 29, 2015, the disclosure of which is hereby incorporated by reference herein in its entirety.

TECHNICAL FIELD

The present invention relates to a device generally to capture an embolus inside a vessel of a living organism, and particularly, to an emboli capture device suitable for use in catheter treatment of a human body.

BACKGROUND ART

Recently, Transcatheter Aortic Valve Implantation (TAVI) that is one of effective treatment methods on aortic stenosis has had the advantage in the respect that open chest surgery is not required and that a burden on a patient is small. In TAVI, an artificial valve is implanted in the aortic valve of the heart, using a catheter by tibiofemoral artery approach and the like. Further, stent graft interpolation of Thoracic Aortic Aneurysm (TAA), similarly, a catheter is inserted from the femoral artery, and a stent graft is disposed on the inner side of the aneurysm. When the embolus such as a thrombus generated in the catheter treatment enters the left common carotid artery directly from the aorta and/or enters the right common carotid artery via the brachiocephalic artery, the embolus may be a cause of causing serious encephalopathy such as cerebral infarction.

In order to reduce the risk of such encephalopathy and/or prevent encephalopathy from occurring, in performing TAVI, such a method is known that a filter to capture an embolus is disposed in the left common carotid artery and the brachiocephalic artery or the right common carotid artery (for example, see Patent Document 1). According to Patent Document 1, in some Embodiment, two filter devices having respective individual filter elements are delivered to the left common carotid artery and the right common carotid artery through a common catheter or individual catheter. In another Embodiment, a proximal filter element and distal filter element are attached to a common guide structure, an opening portion of each filter element is oriented toward a respective inflow direction, the distal filter element is delivered to the left common carotid artery through the right subclavian artery, and the proximal filter element is disposed in the brachiocephalic artery. Further, in another Embodiment, a single filter structure is disposed along the aortic arch so that a part on its front end side is disposed in the left common carotid artery and that a part on the base end side is disposed in the brachiocephalic artery or the right common carotid artery.

PRIOR ART DOCUMENT

Patent Document

Patent Document 1: Published Japanese Patent Translation No. 2011-525405

DISCLOSURE OF INVENTION

Problems to be Solved by the Invention

However, in conventional techniques described in Patent Document 1, there is the following problem. First, in the case of delivering two filter devices using the common catheter, the used catheter needs to have a large tube diameter, and therefore, it is difficult to insert from the radial vein such that the burden on a patient is the lightest and that the risk of a complication is few. Therefore, the catheter is usually inserted from the brachial artery, and needling in the brachial artery enables hemostasis after surgery to be provided relatively for a short time, but there are problems such that nerves exist near the brachial artery, and that the occurrence rate of a complication is slightly high as compared with the femoral artery.

Next, in the filter device where the proximal filter element and distal filter element are attached to the common guide structure, the guide structure is comprised of a signal continuous over tube internally provided with a core wire to drive the filter element between a delivery configuration and a placement configuration, and the proximal filter element and distal filter element are attached to the outer surface of the over tube to be foldable.

Since the brachiocephalic artery and left common carotid artery are branched off from the aortic arch substantially at the right angle, the over tube needs to curve largely to extend from the brachiocephalic artery to the left common carotid artery via the aortic arch. However, the over tube is inserted into a delivery catheter to thereby operate the core wire so as to drive the filter element, therefore needs hardness to some extent along the axis direction, and as a result, is relatively low in flexibility.

Therefore, it is difficult to insert the over tube in the left common carotid artery from the brachiocephalic artery via the aortic arch smoothly and promptly, and some experience is required to operate the tube. Further, there is the risk that the over tube curved largely inside the aortic arch strongly contacts the blood vessel wall to damage, and rather generates many thrombi. Further, when the largely curved over tube exists inside the aortic arch, there is the risk that the tube interferes in performing catheter treatment via the aortic arch.

Further, also in the configuration where the single filter structure is disposed along the aortic arch from inside the brachiocephalic artery to inside the right common carotid artery, the filter structure occupies large space inside the aortic arch. Therefore, there is the risk that delivery of the catheter through the aortic arch is made difficult in operations of TAVI and the like, and that smooth delivery of an artificial valve is prevented.

Therefore, the present invention was made to solve the above-mentioned conventional problems, and it is an object of the invention to provide a minimally invasive emboli capture device which is particular suitable for use in catheter treatment of TAVI and the like, minimizes the influence of an embolus to the brain, and makes the burden on a patient lighter.

Further, it is an object of the present invention to provide an emboli capture device without the risk for interfering with smooth operation of the catheter treatment.

Means for Solving the Problem

In order to solve such problems, the present invention is characterized in that an emboli capture device to capture an embolus inside a vessel is provided with an elongated shaft member having a proximal filter wire portion, a distal filter wire portion, and an intermediate coil wire portion with flexibility between the proximal filter wire portion and the distal filter wire portion, a proximal filter portion that is disposed in the proximal filter wire portion and has a contracted configuration for being delivered to a position inside the vessel and an expanded configuration for capturing an embolus inside the vessel, and a distal filter portion that is disposed in the distal filter wire portion and that has a contracted configuration for being delivered to a position inside the vessel and an expanded configuration for capturing an embolus inside the vessel, the proximal filter portion has a proximal filter body with an inlet opening portion for taking in the embolus inside the vessel in the expanded configuration opened toward the distal side, and that the distal filter portion has a distal filter body with an inlet opening portion for taking in the embolus inside the vessel in the expanded configuration opened toward the proximal side.

In the case where the proximal and distal filter portions thus provided in a single shaft member are respectively disposed inside two downstream vessels branched off from the upstream vessel, by placing the intermediate coil wire portion with flexibility in a path extending from one of the downstream vessels to the other downstream vessel passing the upstream vessel, even when the vessels are connected at a sharp angle, it is possible to place so as not to strongly contact the inner wall of the vessel to press or damage the wall, or so as not to generate an embolus thereby, and it is possible to obtain excellent minimally invasive characteristics.

Accordingly, for example, when the emboli capture device of the present invention is used in catheter treatment such as TAVI and TAA, the proximal and distal filter portions are disposed in the brachiocephalic artery and the left common carotid artery, and it is thereby possible to perform the operation with the influence of the embolus to the brain minimized. Further, the single emboli capture device provided with two filter portions in the shaft member is capable of being inserted from a relatively thin vessel such as the radial artery, and it is thereby possible to make the burden on a patient lighter.

Further, the intermediate coil wire portion neither curves largely inside the upstream vessel nor occupies large space. Accordingly, for example, in performing catheter treatment such as TAVI and TAA through the upstream vessel, the device resolves or reduces the risk that the smooth operation is interfered by existence of the intermediate coil wire portion, and has the advantage.

In some Embodiment, the proximal filter body has a mesh structure comprised of wires having elasticity or shape memory property, further has tie portions on the proximal side and on the distal side for respectively tying the wires at the proximal end and the distal end of the proximal filter body, and with the tie portion on the proximal side fixed to the proximal filter wire portion, is capable of shifting to be the contracted configuration when the tie portion on the distal side shifts to the distal side along the proximal filter wire portion, and to be the expanded configuration when the tie portion on the distal side shifts to the proximal side, and the distal filter body has a mesh structure comprised of wires having elasticity or shape memory property, further has tie portions on the proximal side and on the distal side for respectively tying the wires at the proximal end and the distal end of the distal filter body, and with the tie portion on the proximal side fixed to the distal filter wire portion, is capable of shifting to be the contracted configuration when the tie portion on the distal side shifts to the distal side along the distal filter wire portion, and to be the expanded configuration when the tie portion on the distal side shifts to the proximal side.

The tie portions at the distal end of the proximal and distal filter bodies are made movable, and therefore, also in a state of capturing emboli inside the proximal and distal filter bodies, the proximal and distal filters are capable of changing to the contracted configuration easily and smoothly, in storing the emboli capture device in the delivery catheter from a placement position inside the vessel.

Further, in some Embodiment, the proximal filter wire portion has a stopper member that limits a shift of the tie portion on the distal side of the proximal filter body along the proximal filter wire portion, and the distal filter wire portion has a stopper member that limits a shift of the tie portion on the distal side of the distal filter body along the distal filter wire portion. By thus limiting the shift of the tie portion on the distal side of each of the proximal and distal filter bodies by the stopper member, it is possible to suppress so that the proximal and distal filter bodies are not expanded more than a certain amount.

In another Embodiment, the proximal filter body has a mesh structure comprised of wires having elasticity or shape memory property, further has tie portions on the proximal side and on the distal side for respectively tying the wires at the proximal end and the distal end of the proximal filter body, and with the tie portion on the proximal side fixed to the proximal filter wire portion, is capable of shifting to be the contracted configuration when the tie portion on the distal side shifts to the distal side along the proximal filter wire portion, and to be the expanded configuration when the tie portion on the distal side shifts to the proximal side, the distal filter body has a mesh structure comprised of wires having elasticity or shape memory property, further has tie portions on the proximal side and on the distal side for respectively tying the wires at the proximal end and the distal end of the distal filter body, and is capable of shifting to be the contracted configuration when the tie portions on the proximal side and on the distal side separate from each other along the distal filter wire portion, and to be the expanded configuration when the tie portions approach each other, and the distal filter wire portion has a stopper member that limits a shift to the distal side of the proximal-side tie portion of the distal filter body along the distal filter wire portion, and a shift to the proximal side of the distal-side tie portion.

The distal filter body is thus made movable along the distal filter wire portion in some distance range limited by the stopper member, and therefore, after once placing the distal filter portion inside the vessel, it is possible to adjust or change the position of placement, corresponding to a body type and shape of the body of the patient, and various circumstances in the medical field.

Further, in another Embodiment, the shaft member further has a front end guide portion with flexibility on the distal side of the distal filter wire portion. By this means, the emboli capture device is capable of proceeding smoothly inside the delivery catheter by being guided by the front end guide portion.

BEST MODE FOR CARRYING OUT THE INVENTION

With reference to accompanying drawings, suitable Embodiments of an emboli capture device according to the present invention will be described below in detail, in the case of applying to a filter device used in TAVI.

Figure 1:
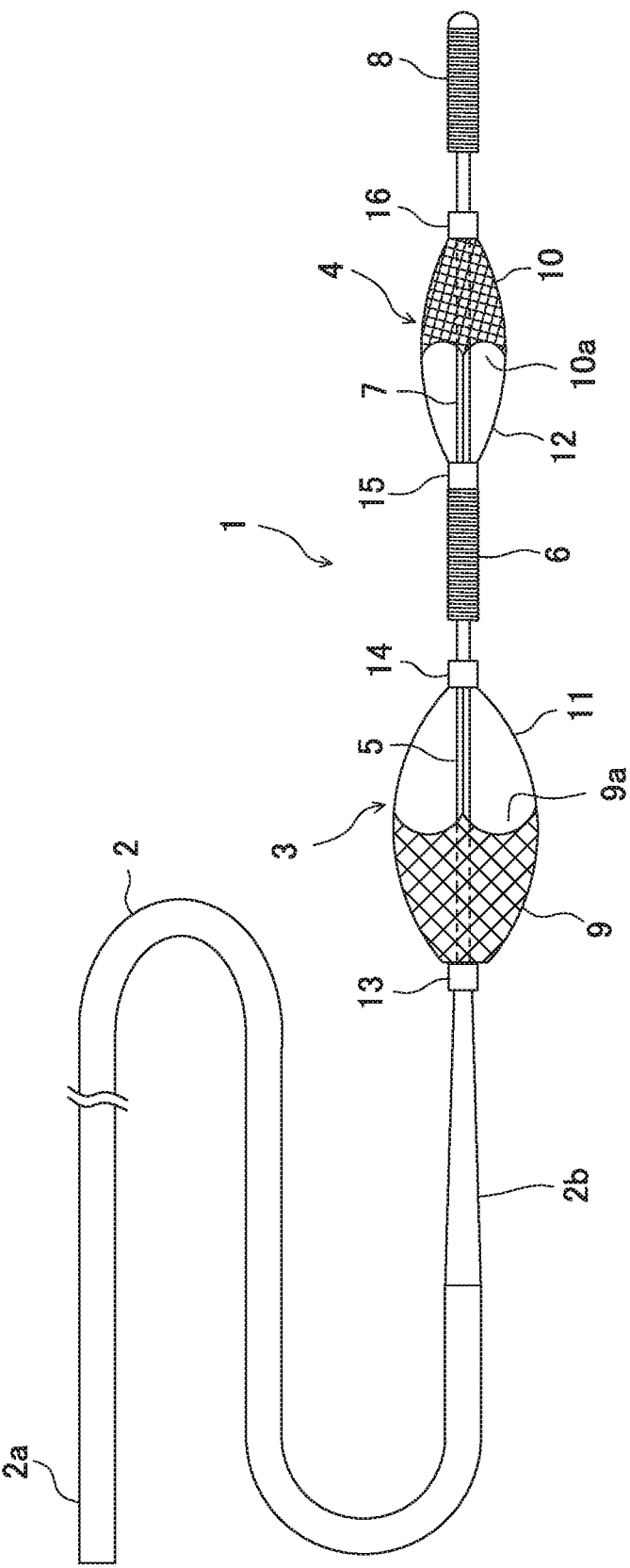
FIG. 1 is an entire schematic view illustrating a suitable Embodiment of a filter device according to the present invention.

As shown in FIG. 1, a filter device 1 of this Embodiment is provided with an elongated shaft 2, and a proximal filter 3 and distal filter 4 disposed on the front end side of the shaft. In order to move to a desired position inside the vessel through appropriate guide means such as a delivery catheter and operate at its base end 2a, the shaft 2 is comprised of a thin flexible wire as a whole. As materials of such a shaft 2, for example, metal materials such as nickel titanium-based alloy well known as Nitinol (Trade Name) and stainless steel are suitable.

On the front end side provided with the filter of the shaft 2, a thinner distal filter wire portion 5 with the diameter reduced from the base end side via a taper portion 2b, an intermediate coil wire portion 6, and a distal filter wire portion 7 with the same diameter as the proximal filter wire portion are provided successively. At the front end of the distal filter wire portion 7 is further provided a front end coil wire portion 8 for a guide.

The intermediate coil wire portion 6 and front end coil wire portion 8 have the structure conventionally publicly known, are obtained by winding and plaiting thin coil wires to cover a wire portion with a thinner diameter than the proximal and distal filter wire portions 5, 7 as a core material, and exhibit higher flexibility than both of the filter wire portions. In the case where the front end coil wire portion 8 is comprised of radio-opaque materials, for example, such as platinum and tungsten, it is possible to check the position and posture under X-ray illumination in an operation, and such a case is advantageous.

In FIG. 1, each of the proximal filter 3 and distal filter 4 is expressed in a configuration where each filter is expanded in the radius direction of the shaft 2 to capture an embolus. In the expanded configuration, the proximal and distal filters have proximal and distal filter bodies 9, 10 opened in the shape of a parachute, and support portions 11, 12 in the shape of a plurality of strings extending from respective outer edges of the proximal and distal filter bodies to the proximal and distal filter wire portions 5, 7, respectively.

The proximal filter 3 is oriented so that an inlet opening portion 9a of the proximal filter body 9 faces the distal side i.e. distal filter 4 side. The distal filter 4 is oriented so that an inlet opening portion 10a of the distal filter body 10 faces the proximal side i.e. proximal filter 3 side.

The proximal and distal filter bodies 9, 10 of this Embodiment are formed by plaiting and weaving a plurality of thin flexible wires having elasticity or shape memory property in the shape of a mesh. The support portions 11, 12 are formed by pulling the plurality of plaited or woven wires from the outer edges of the proximal and distal filter bodies every a plurality of wires to tie in the shape of a string.

For the wires constituting the proximal and distal filter bodies 9, 10, conventionally publicly known materials are suitably selected and used. For example, among suitable materials are nickel titanium-based alloy wire, titanium wire, complex materials of platinum or gold wire and nickel titanium-based alloy wire, gold-plated nickel wire, titanium-based alloy wire and the like.

By thus forming, the proximal and distal filter bodies are capable of capturing emboli such as thrombi flowing inside the blood vessel, while passing a blood flow inside the blood vessel. Further, it is possible to contract or deform the proximal and distal filter bodies in the radius direction from the expanded configuration with ease, and restore to the expanded configuration again.

In the base end-side end portion of the proximal filter 3, the wires forming the proximal filter body 9 are tied with a tie instrument 13 in the shape of a ring extrapolated to the proximal filter wire portion 5. In the front end-side end portion of the proximal filter, the end portion of the entire support portion 11 is similarly tied with a tie instrument 14 in the shape of a ring extrapolated to the proximal filter wire portion.

The tie instrument 13 on the base end side is fixed to the proximal filter wire portion 5 on its base end side i.e. in the end portion on the side for coupling to the taper portion 2b. The tie instrument 14 on the front end side is provided to be able to slide and shift on the proximal filter wire portion along its axis direction.

By this means, by the tie instrument 14 shifting to the front end side, the proximal filter 3 changes from the expanded configuration shown in FIG. 1 to the contracted configuration where the proximal filter body 9 contracts in the radius direction from the parachute shape and is elongated thin along the proximal filter wire portion 5. Contrary, when the tie instrument 14 shifts from the contacted state to the base end side, the proximal filter 3 returns to the expanded configuration where the proximal filter body 9 is opened in the shape of a parachute of FIG. 1.

Similarly, in the base end-side end portion of the distal filter 4, the end portion of the entire support portion 12 is tied with a tie instrument 15 in the shape of a ring extrapolated to the distal filter wire portion 7. In the front end-side end portion of the distal filter, the wires forming the distal filter body 10 are tied with a tie instrument 16 in the shape of a ring extrapolated to the distal filter wire portion.

The tie instrument 15 on the base end side is fixed to the distal filter wire portion 7 on its base end side i.e. in the end portion on the side for coupling to the intermediate coil wire portion 6. The tie instrument 16 on the front end side is provided to be able to slide and shift on the distal filter wire portion along its axis direction.

By this means, by the tie instrument 16 shifting to the front end side, the distal filter 4 changes from the expanded configuration shown in FIG. 1 to the contracted configuration where the distal filter body 10 contracts in the radius direction from the parachute shape and is elongated thin along the distal filter wire portion 7. Contrary, when the tie instrument 16 shifts from the contacted state to the base end side, the distal filter 4 returns to the expanded configuration where the distal filter body 10 is opened in the shape of a parachute of FIG. 1.

For tie instruments 13 to 16, it is preferable to use radio-opaque metal materials, for example, such as platinum and tungsten. By this means, it is possible to check the position of each of the tie instruments under X-ray illumination in an operation.

Figure 2:
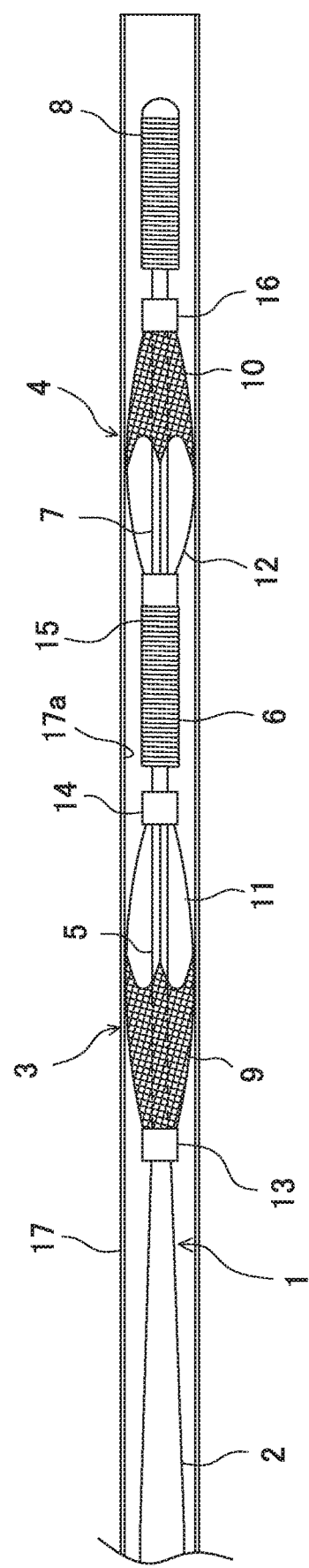
FIG. 2 is a cross-sectional view illustrating a state in which the filter device of FIG. 1 is inserted into a delivery catheter.

FIG. 2 illustrates a state in which the filter device 1 of FIG. 1 is inserted into a delivery catheter 17 with an inside diameter sufficiently smaller than the maximum outside diameter in its expanded configuration. At this point, the proximal and distal filters 3, 4 are long slender contracted configurations along the filter wire portion, where the proximal and distal filter bodies 9, 10 are pressed against an inner wall 17a of the delivery catheter 17 and contract in the radius direction, and concurrently the movable tie instruments 14, 16 on the front end side respectively slide on the filter wire portions 5, 7 to the front end side.

In using, the filter device 1 is inserted, from its front end, into the delivery catheter 17, from its base end, early delivered to inside the vessel of the patient, and is moved to a predetermined position along the delivery catheter. Alternatively, in a state in which the filter device 1 is beforehand inserted from its front end and is stored, the delivery catheter 17 is delivered to a predetermined position inside the vessel of the patient. In either case, when the proximal and distal filters 3, 4 are released inside the vessel from the delivery catheter, the proximal and distal filter bodies 9, 10 automatically expand in the radius direction, while sliding the movable tie instruments 14, 16 to the base end side, by elasticity or shape memory property of the wires forming the bodies 9, 10, respectively.

The case of using the filter device 1 of FIG. 1 in TAVI will specifically be described below using FIGS. 3 to 7. This Embodiment applies an approach method of passing the filter device 1 through the radial artery from an incision formed in the wrist of the patient to insert.

Figure 3:
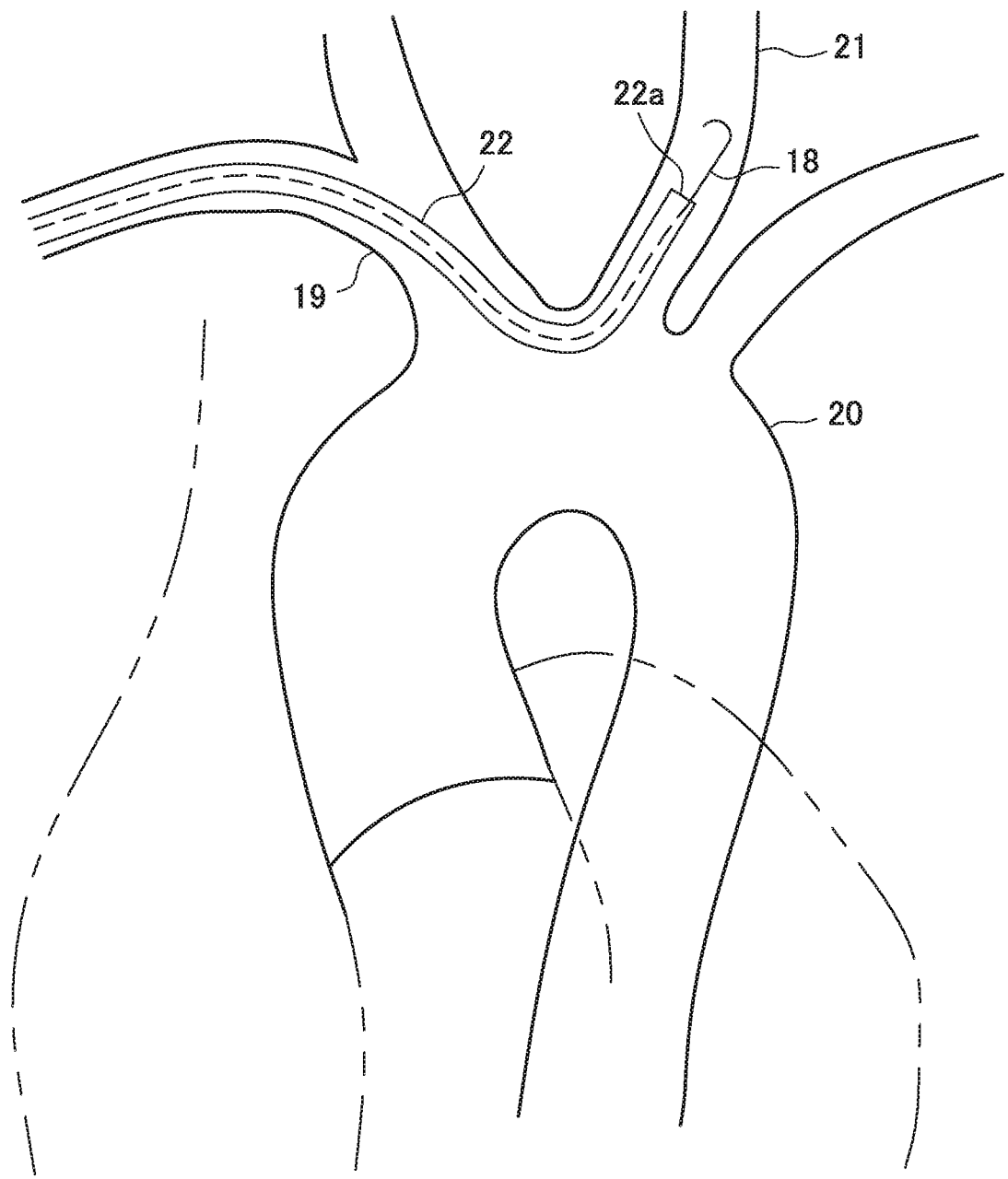
FIG. 3 is a schematic view to explain process to place the filter device of FIG. 1.

First, in FIG. 3, a guide wire 18 is inserted in the radial artery from the incision, and its front end is moved into the left common carotid artery 21 via the brachiocephalic artery 19 and the aortic arch 20. Next, as shown in the figure, a delivery catheter 22 comprised of a micro catheter is extrapolated to the guide wire 18 from its base end, and is delivered so that its front end opening 22a is positioned inside the left common carotid artery 21. Subsequently, the guide wire 18 is removed from the delivery catheter 22.

The filter device 1 is inserted, from its front end, into the delivery catheter 22 thus placed inside the blood vessel, from its base end opening. The filter device 1 is moved to near the front end of the delivery catheter 22 with the proximal and distal filters 3, 4 kept in the contracted configuration shown in FIG. 2. At this point, the filter device 1 is guided by the front end coil wire portion 8, and is capable of moving inside the delivery catheter 22 smoothly.

Figure 4:
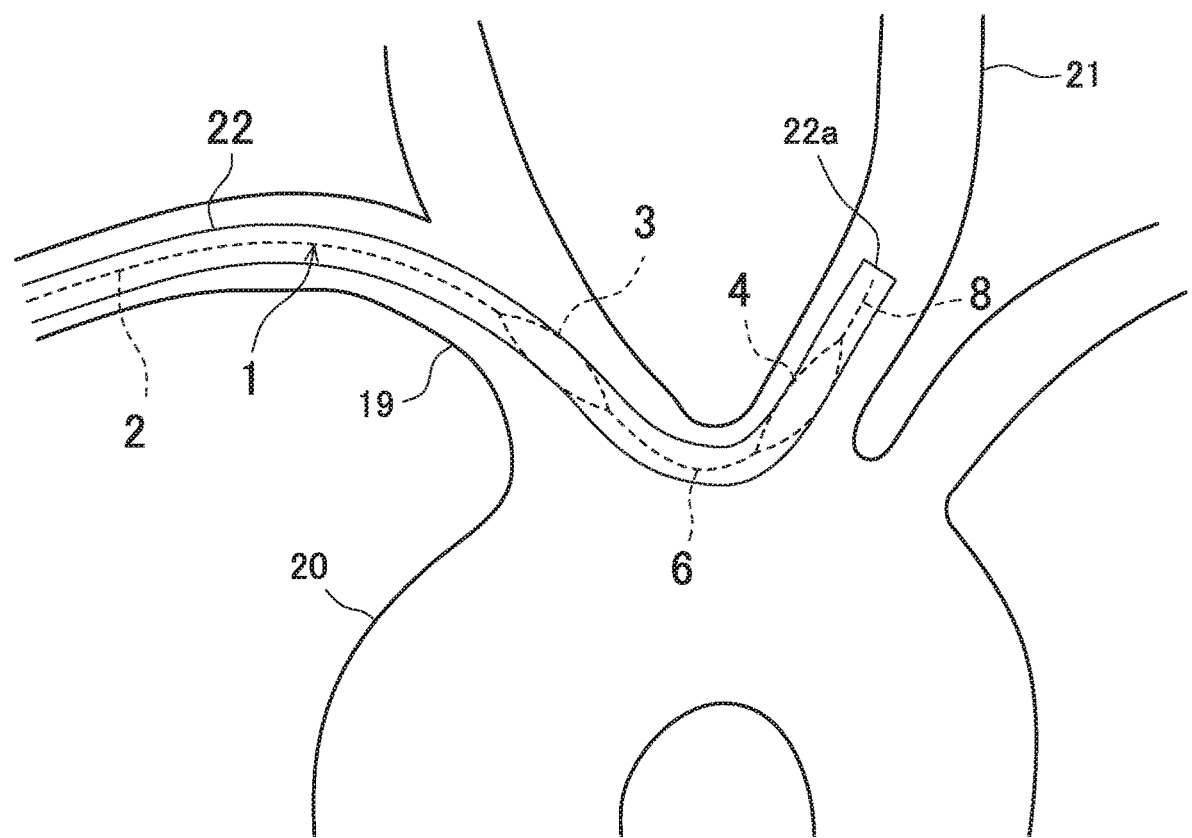
FIG. 4 is a schematic view to explain the process to place the filter device of FIG. 1.
Figure 5:
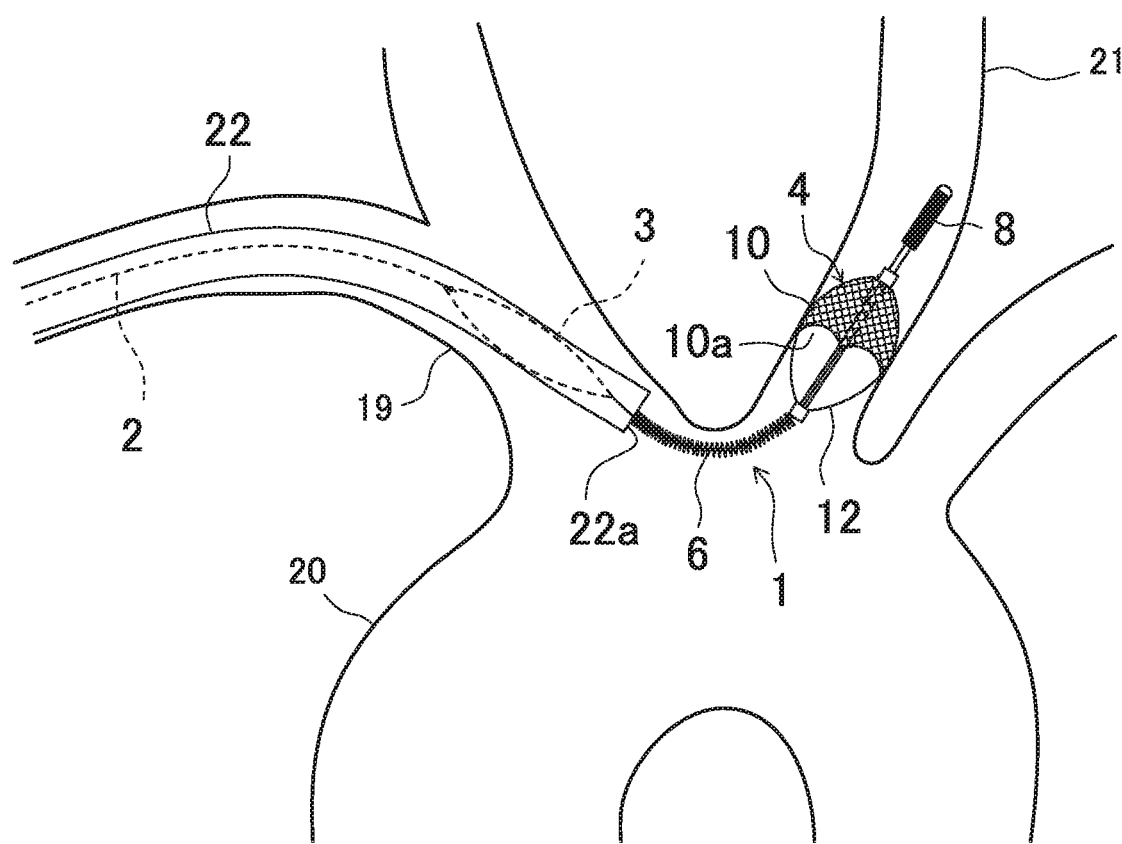
FIG. 5 is a schematic view to explain the process to place the filter device of FIG. 1.

As shown in FIG. 4, in the filter device 1, the distal filter 4 is positioned inside the left common carotid artery 21, the proximal filter 3 is positioned inside the brachiocephalic artery 19, and the intermediate coil wire portion 6 is moved to a position extended between the brachiocephalic artery 19 and the left common carotid artery 21 passing the aortic arch 20. Next, as shown in FIG. 5, only the delivery catheter 22 is pulled to the base end side so that the distal filter 4 is drawn to the left common carotid artery 21 from the front end opening 22a. The distal filter released from the delivery catheter 22 automatically becomes the expanded configuration of FIG. 1 from the contracted configuration inside the left common carotid artery 21.

Further, only the delivery catheter 22 is moved back to the base end side, so that the intermediate coil wire portion 6 is drawn inside the aortic arch 20, and that the proximal filter 3 is drawn inside the brachiocephalic artery 19. The distal filter released from the delivery catheter 22 automatically becomes the expanded configuration of FIG. 1 from the contracted configuration inside the brachiocephalic artery 21.

Figure 6:
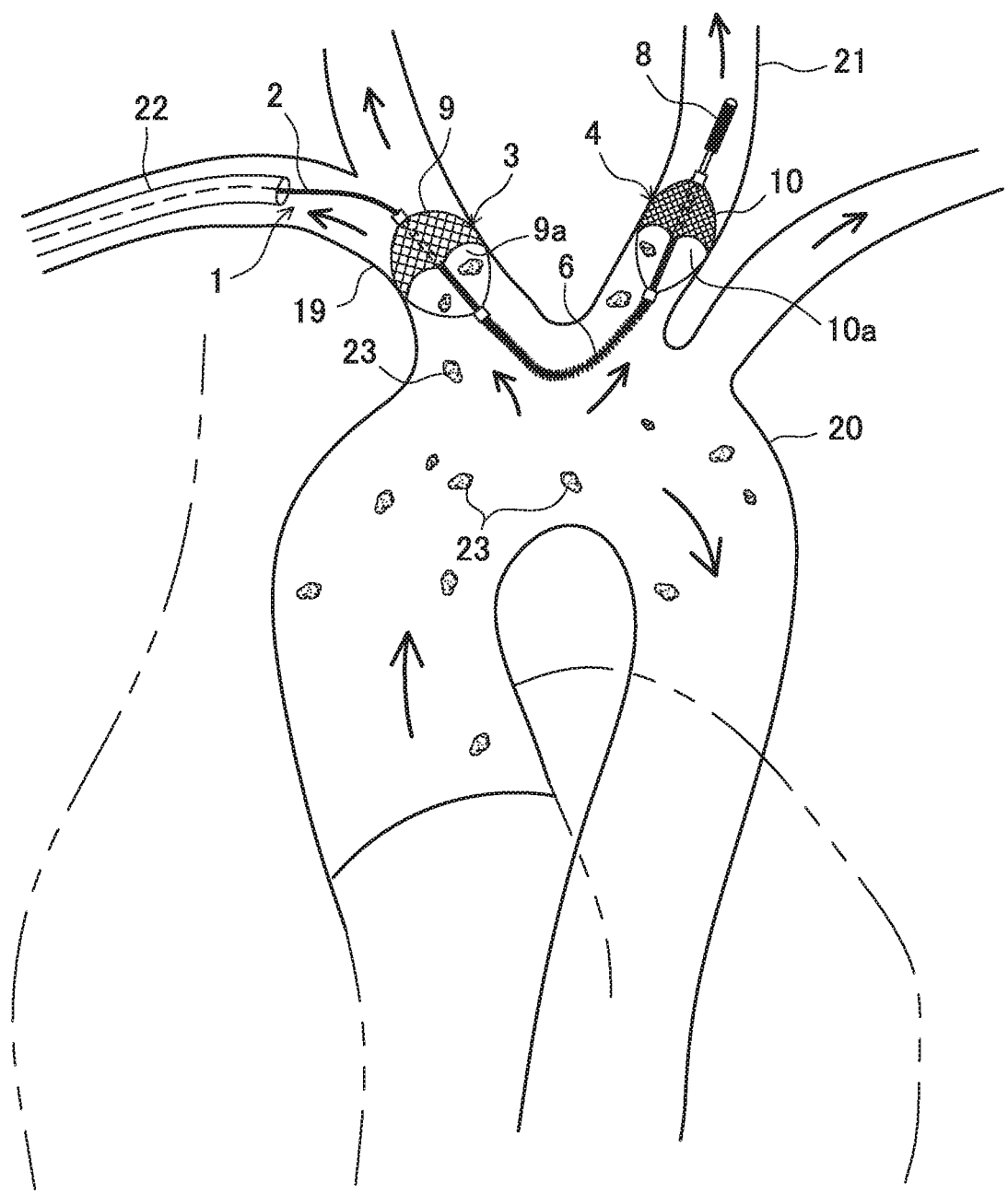
FIG. 6 is a schematic view to explain the process to place the filter device of FIG. 1.

Thus, as shown in FIG. 6, in the filter device 1, the distal filter 4 is disposed inside the left common carotid artery 21, the proximal filter 3 is disposed inside the brachiocephalic artery 19, and the intermediate coil wire portion 6 is disposed so as to extend between the brachiocephalic artery 19 and the left common carotid artery 21 passing the aortic arch 20. Such an arrangement of the filter device 1 is adjusted by operating the base end 2a of the shaft 2.

In the distal filter 4, the distal filter body 10 is placed so that the inlet opening 10a faces the aortic arch 20 side, and that the parachute shape is adapted to the inner wall of the left common carotid artery 21. Concurrently, in the proximal filter 3, the proximal filter body 9 is placed so that the inlet opening 9a faces the aortic arch 20 side, and that the parachute shape is adapted to the inner wall of the brachiocephalic artery 19. By this means, it is possible to reliably capture emboli 23 such as thrombi inside the blood flow flown into the brachiocephalic artery 19 and the left common carotid artery 21 from the aortic arch 20 upstream, while ensuring the blood flow.

The intermediate coil wire portion 6 has sufficient flexibility, and thereby curves and passes through each coupling portion of the aortic arch 20, and the brachiocephalic artery 19 and the left common carotid artery 21 at a severe angle close to substantially the right angle along the shape of the coupling portion. Since the intermediate coil wire portion 6 does strongly not contact the inner walls of the aortic arch 20, the brachiocephalic artery 19 and the left common carotid artery 21, the risk of damaging the inner wall of the blood vessel and generating thrombi is extremely low, as compared with conventional techniques. Further, the risk is extremely low that the existence of the intermediate coil wire portion 6 subsequently interferes with smooth operation of TAVI inside the aortic arch 20.

After the operation of TAVI, the delivery catheter 22 is moved again along the filter device 1, and the proximal filter 3 and distal filter 4 are sequentially collected in the catheter 22. At this point, by being pressed by the front end opening 22a of the delivery catheter, the proximal and distal filter bodies 9, 10 become the contracted configurations shown in FIG. 2 and are stored, while holding the captured emboli inside. As described above, since the tie instruments 14, 16 on the front end side are made slidable, the proximal and distal filters 3, 4 deform to the contracted configurations with ease, also in a state of capturing emboli inside the proximal and distal filter bodies.

It is possible to draw the filter device 1 from the blood vessel of the patient, while being stored in the delivery catheter 22. Further, it is also possible to first collect the filter device 1 from the delivery catheter, and subsequently draw the delivery catheter from the blood vessel of the patient.

Figure 7:
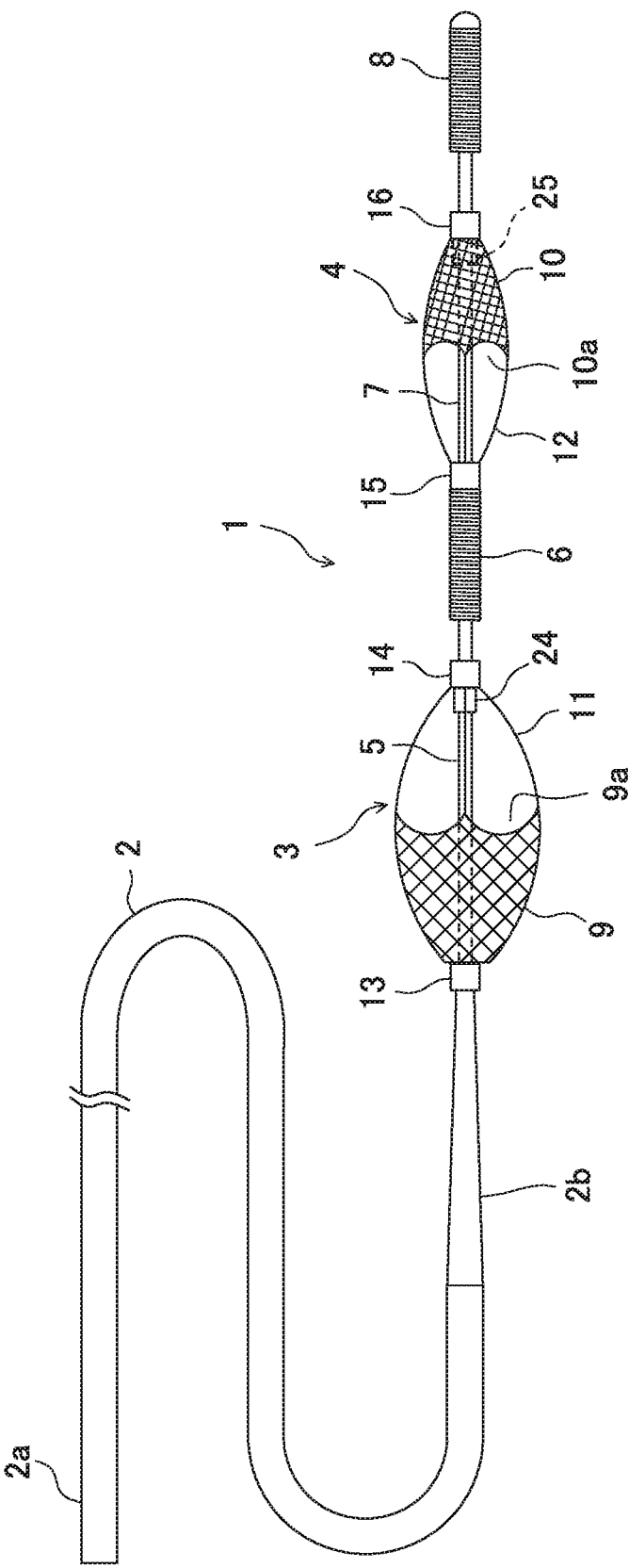
FIG. 7 is an entire schematic view illustrating a Modification of the filter device of FIG. 1.
Figure 8:
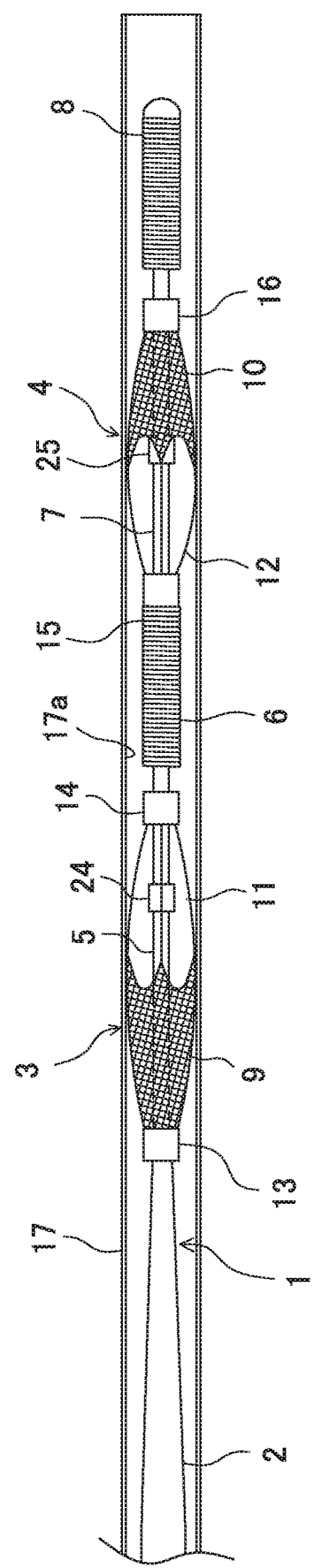
FIG. 8 is a cross-sectional view illustrating the Modification of FIG. 7 inserted into a delivery catheter.

In a Modification of this Embodiment, as shown in FIGS. 7 and 8, it is possible to provide stopper members 24, 25 on the proximal and distal filter wires 5, 7. The stopper members 24, 25 are fixed in between the tie instruments 13, 14 of the proximal filter 3, and in between the tie instruments 15, 16 of the distal filter 4, respectively, and limit shift ranges of the slidable tie instruments 14, 16 on the distal side to the base end side. By this means, it is possible to suppress so that the proximal and distal filter bodies 9, 10 expand more than a certain amount.

When the filter body is opened excessively, there is the risk that the body is easy to shift from a desired position inside the blood vessel, and that emboli such as thrombi are newly generated by contact with the inner wall of the blood vessel in shifting. In this Modification, by providing the stopper members 24, 25, expansion of the proximal and distal filter bodies 9, 10 is suppressed, and it is thereby possible to prevent unsuitable shifts inside the blood vessel and generation of emboli.

When the filter device 1 of the present invention is used in TAVI, there is the case where a distance between an entrance of the brachiocephalic artery 19 and an entrance of the left common carotid artery passing the aortic arch 20 differs corresponding to a body type and shape of the body of the patient. Further, there is the case where the position inside the artery to place the proximal filter 3 and/or the distal filter 4 differs corresponding to the patient and circumstances. Therefore, it is preferable to beforehand prepare a plurality of types of filter devices 1 with different lengths of the proximal filter wire portion 5, the intermediate coil wire portion 6 and/or the distal filter wire portion 7. However, actually, the case may arise that the position to finally place is adjusted or changed, after releasing the distal filter 4 from the delivery catheter 22 into the left common carotid artery 21.

Therefore, in another Modification of the present invention, modifications are added to the filter device 1 shown in FIGS. 7 and 8, it is possible to provide the distal filter 4 to be able to shift in some distance range along the distal filter wire portion 7. More specifically, both the tie instruments 15, 16 on the proximal side and on the distal side of the distal filter 4 are provided to be slidable with respect to the distal filter wire portion 7, and the stopper member 25 is fixed onto the distal filter wire portion 7 between both the tie instruments 15, 16. By this means, the distal filter 4 is held to be able to shift along the distal filter wire portion 7, in a range where the stopper member 25 limits a shift to the distal side of the proximal side tie instrument 15, and further limits a shift to the proximal side of the distal side tie instrument 16.

In this Embodiment, a single stopper member 25 is only provided to respectively limit shifts of both of the tie instruments 15, 16 on the distal filter wire portion 7. In another Embodiment, it is possible to provide the stopper member for the proximal side tie instrument 15 and the stopper member for the distal side tie instrument 16 separately. In this case, it is possible to set the shift range of the distal filter 4 more specifically in various manners.

In the distal filter 4, after releasing from the delivery catheter 22 and once placing inside the left common carotid artery 21, the placement position is adjusted and changed, by operating the shaft 2 from its base end side. For example, in the case of desiring to place the distal filter 4 more backward in the left common carotid artery 21, the shaft 2 is sent to the distal side to bring the stopper member 25 into contact with the distal side tie instrument 16, the member is pushed to the distal side, and the distal filter 4 is shifted to a backward position. Contrary, in the case of desiring to return the distal filter 4 to the entrance side of the left common carotid artery 21, the shaft 2 is pulled to the proximal side to bring the stopper member 25 into contact with the proximal side tie instrument 15, the member is pulled back to the proximal side, and the distal filter 4 is shifted to a position on the entrance side.

Further, in pushing the distal side tie instrument 16 to the distal side by the stopper member 25, the force acts in the direction for deforming the distal filter body 10 to contract from the expanded state. Similarly, in pulling the proximal side tie instrument 15 back to the proximal side by the stopper member 25, the force acts in the direction for deforming the distal filter body 10 to contract from the expanded state via the support portion 12. Accordingly, the risk is extremely low that a shift of the once placed distal filter 4 damages or has an adverse effect on the inner wall of the left common carotid artery 21, and that the shift itself of the distal filter 4 is difficult.

Thus, in addition to features of the present invention described above in relation to the filter devices 1 of FIGS. 1 and 7, in this Embodiment, it is possible to adjust the placement position of the distal filter 4 optimally, without providing the blood vessel or another vessel with damage and adverse effect, corresponding to various situations or circumstances related to a difference in the distance between the entrance of the brachiocephalic artery 19 and the entrance of the left common carotid artery, and the placement position of the proximal filter 3 and/or the distal filter 4. Moreover, it is possible to further decrease types of lengths of the proximal filter wire portion 5, the intermediate coil wire portion 6 and/or the distal filter wire portion 7, which should be prepared in advance. These respects mean that it is possible to always respond as circumstances demand in the medical field using the filter device 1, and also in this respect, the device is significantly advantageous.

This Embodiment describes the case of using the filter device 1 of the present invention in TAVI, and the invention is applicable also to TAA for similarly performing procedures inside the aorta. Further, the present invention is capable of being used in blood vessels other than the brachiocephalic artery and left common carotid artery branched off from the aorta or any vessels such as lymphatic vessels.

The present invention is not limited to the above-mentioned Embodiments, and is capable of being carried into practice with various modifications • changes added to the above-mentioned Embodiments within the technical scope of the invention. For example, it is possible to coat the surface of the shaft and/or each filter constituting the filter device with proper agents. Particularly, in the case of applying hydrophilic coating, since lubricant properties are exerted by contacting the blood, operation for introducing into the blood vessel is made easy.

DESCRIPTION OF THE SYMBOLS

1 Filter device
2 Shaft
3 Proximal filter
4 Distal filter
5 Proximal filter wire portion
6 Intermediate coil wire portion
7 Distal filter wire portion
8 Front end coil wire portion
9 Proximal filter body
10 Distal filter body
11, 12 Support portion
13-16 Tie instrument
17, 22 Delivery catheter
18 Guide wire
19 Brachiocephalic artery
20 Aortic arch
21 Left common carotid artery
23 Embolus

The invention claimed is:

1. An emboli capture device for capturing emboli in a vessel, comprising:
an elongate shaft member including a proximal filter wire portion, an intermediate coil wire portion, and a distal filter wire portion, continuously provided in order toward a distal end thereof;
a proximal filter portion provided on the proximal filter wire portion, and having a contracted configuration for being delivered to a site within the vessel and an expanded configuration for capturing emboli within the vessel; and
a distal filter portion provided on the distal filter wire portion, and having a contracted configuration for being delivered to a site within the vessel and an expanded configuration for capturing emboli within the vessel,
wherein the proximal filter portion includes a proximal filter body having an inlet opening to be opened toward a distal side of the proximal filter portion for capturing emboli within the vessel in the expanded configuration, and the distal filter portion includes a distal filter body having an inlet opening to be opened toward a proximal side of the distal filter portion for capturing emboli within the vessel in the expanded configuration,
the intermediate coil wire portion has flexibility higher than the proximal filter wire portion and the distal filter wire portion,
the proximal filter body has a mesh structure comprising wires having elasticity or a shape memory property, the wires being tied at a proximal end of the proximal filter body into a proximal tie portion which is fixed to the proximal filter wire portion, and the wires, forming a support portion of the proximal filter body, being tied at a distal end of the proximal filter body into a distal tie portion which is moveable along the proximal filter wire portion so that the proximal filter body is in the contracted configuration when the distal tie portion moves toward a distal side of the proximal filter body, and is in the expanded configuration when the distal tie portion moves toward a proximal side of the proximal filter body, and
the distal filter body has a mesh structure comprising wires having elasticity or a shape memory property, the wires, forming a support portion of the distal filter body, being tied at a proximal end of the distal filter body into a proximal tie portion which is fixed to the distal filter wire portion, and the wires being tied at a distal end of the distal filter body into a distal tie portion which is moveable along the distal filter wire portion so that the distal filter body is in the contracted configuration when the distal tie portion moves toward a distal side of the distal filter body, and is in the expanded configuration when the distal tie portion moves toward a proximal side of the distal filter body.

2. The emboli capture device as described in claim 1, wherein the proximal filter wire portion has a stopper member that limits movement of the distal tie portion of the proximal filter body along the proximal filter wire portion, and the distal filter wire portion has a stopper member that limits movement of the distal tie portion of the distal filter body along the distal filter wire portion.

3. An emboli capture device for capturing emboli in a vessel, comprising:
an elongate shaft member including a proximal filter wire portion, an intermediate coil wire portion, and a distal filter wire portion, continuously provided in order toward a distal end thereof;
a proximal filter portion provided on the proximal filter wire portion, and having a contracted configuration for being delivered to a site within the vessel and an expanded configuration for capturing emboli within the vessel; and
a distal filter portion provided on the distal filter wire portion, and having a contracted configuration for being delivered to a site within the vessel and an expanded configuration for capturing emboli within the vessel,
wherein the proximal filter portion includes a proximal filter body having an inlet opening to be opened toward a distal side of the proximal filter portion for capturing emboli within the vessel in the expanded configuration, and the distal filter portion includes a distal filter body having an inlet opening to be opened toward a proximal side of the distal filter portion for capturing emboli within the vessel in the expanded configuration,
the intermediate coil wire portion has flexibility higher than the proximal filter wire portion and the distal filter wire portion,
the proximal filter body has a mesh structure comprising wires having elasticity or a shape memory property, the wires being tied at a proximal end of the proximal filter body into a proximal tie portion which is fixed to the proximal filter wire portion, and the wires, forming a support portion of the proximal filter body, being tied at a distal end of the proximal filter body into a distal tie portion which is moveable along the proximal filter wire portion so that the proximal filter body is in the contracted configuration when the distal tie portion moves toward a distal side of the proximal filter body, and is in the expanded configuration when the distal tie portion moves toward a proximal side of the proximal filter body,
the distal filter body has a mesh structure comprising wires having elasticity or a shape memory property, the wires, forming a support portion of the distal filter body, being tied at a proximal end of the distal filter body into a proximal tie portion and the wires being tied at a distal end of the distal filter body into a distal tie portion, the proximal tie portion and the distal tie portion being moveable along the distal filter wire portion so that the distal filter body is in the contracted configuration when the proximal tie portion and the distal tie portion move apart from each other, and is in the expanded configuration when the proximal tie portion and the distal tie portion move closer to each other, and
the distal filter wire portion is provided with a stopper member to limit movement of the proximal tie portion of the distal filter body toward a distal side of the distal filter body and movement of the distal tie portion toward a proximal side of the distal filter body along the distal filter wire portion.

4. The emboli capture device as described in claim 1, wherein the elongated shaft member further has a front end guide portion with flexibility at a front end of the distal filter wire portion.

5. The emboli capture device as described in claim 1, further comprising one micro catheter into which the elongate shaft member is inserted with the proximal and distal filter portions in the contracted configuration.

6. The emboli capture device as described in claim 3, wherein the stopper member is fixed on the elongate shaft member and is arranged between the proximal tie portion and the distal tie portion of the distal filter portion such that the distal filter body moves in a range between positions where the proximal tie portion of the distal filter portion contacts the stopper member and where the distal tie portion of the distal filter portion contacts the stopper member.

7. The emboli capture device as described in claim 3, wherein the elongated shaft member further has a front end guide portion with flexibility at a front end of the distal filter wire portion.

8. The emboli capture device as described in claim 3, further comprising one micro catheter into which the elongate shaft member is inserted with the proximal and distal filter portions in the contracted configuration.

* * * * *